United States Patent
Hui et al.

(10) Patent No.: US 6,991,805 B1
(45) Date of Patent: *Jan. 31, 2006

(54) TEMPERATURE SENSITIVE CONTROL OF LIPOSOME-CELL ADHESION

(75) Inventors: Sek Wen Hui, Williamsville, NY (US); Arindam Sen, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 232 days.

This patent is subject to a terminal disclaimer.

(21) Appl. No.: 10/236,345

(22) Filed: Sep. 6, 2002

(51) Int. Cl.
*A61K 9/127* (2006.01)

(52) U.S. Cl. ............... 424/450; 424/1.21; 424/9.321; 424/9.51

(58) Field of Classification Search ............... 424/450, 424/1.21, 9.321, 9.51, 417, 420; 428/402.2
See application file for complete search history.

(56) References Cited

U.S. PATENT DOCUMENTS

| | | | | |
|---|---|---|---|---|
| 5,364,632 A | * | 11/1994 | Benita et al. | 424/450 |
| 5,654,000 A | * | 8/1997 | Poli et al. | 424/450 |
| 5,944,754 A | * | 8/1999 | Vacanti | 623/23.76 |
| 6,143,321 A | * | 11/2000 | Needham et al. | 424/450 |
| 6,525,102 B1 | * | 2/2003 | Chen et al. | 424/85.2 |

OTHER PUBLICATIONS

Hayashi et al, Bioconjugate Chem. vol. 9, pp. 382-389, 1998.*
Bassett et al, The Journal of Urology, vol. 135, pp. 612-615, 1986.*
Alexandridia et al.., *Micellization of Poly (ethylene oxide)-Poly (propylene oxide)-Poly (ethylene oxide) Triblock Copolymers in Aqueous Solutions: Thermodynamics of Copolymer Association*, Macromolecules, 1994, vol. 27, No. 9, pp. 2414-2425.

* cited by examiner

*Primary Examiner*—Gollamudi S. Kishore
(74) *Attorney, Agent, or Firm*—Hodgson Russ LLP; Ranjana Kadle

(57) ABSTRACT

The present invention provides a liposomal composition for targeted delivery of drugs. The composition comprises poloxamer molecules and liposomes encapsulating one or more delivery agents. At above the critical micellar temperature of the poloxamer, a fraction of the poloxamer molecules form micelles and another fraction becomes incorporated into the liposome surface, thereby inhibiting their adhesion to cells. At a temperature below the critical micellar temperature, the poloxamer molecules dissociate into monomers allowing the liposomes to adhere to adjacent cells and effecting retention of the liposomes in the surrounding tissue. A method is provided for delivery of agents to target site comprising administering the composition to an individual and cooling the target site to cause retention of the liposomes at or near the target site.

18 Claims, 5 Drawing Sheets

TEMPERATURE SENSITIVE CONTROL OF LIPOSOME-CELL ADHESION

This invention was made with Government support under grant no. GM 30969 awarded by the National Institutes of Health. The Government has certain rights in the invention.

FIELD OF THE INVENTION

This invention relates generally to the field of drug delivery and more particularly provides a liposomal composition and method for preferential retention of liposomes at or near the target site.

DESCRIPTION OF RELATED ART

Throughout the application, references are cited as numerals with the full citations being provided at the end of Detailed Description of Invention.

Liposomes have been extensively used in the past decade as drug carriers. Desired properties of efficient carriers include the ability to evade the mononuclear phagocyte system (MPS) to prolong the circulation half-life ($t_{1/2}$), and preferential release of the encapsulated drug at the targeted site. Use of sterically stabilized liposomes has increased the liposome circulation time considerably [2,3]. "Stealth" liposomes [1] or "cryptosomes" [2] have been used to improve the efficiency of drug delivery by liposomes. Conventional liposomes are intercepted at an early stage of circulation by the mononuclear phagocyte system (MPS) [3]. Unlike conventional liposomes, "stealth" or sterically stabilized liposomes show reduced uptake by the MPS, thus prolonging their circulation half-life considerably [4–6]. Stealthing of conventional liposomes is done primarily by using polyethylene glycol (PEG) conjugated lipids at different concentrations and compositions [7,8]. The use of PEG conjugated lipids to form stealth liposomes is a well-accepted process. The predecessors of PEG-lipids, namely GM1 ganglioside [5,25] and phospatidylinositol [5,26], though effective in increasing $t_{1/2}$ of the conventional liposomes, did not match the superior shielding ability of PEG-lipids. Moreover, being a synthetic lipid, PEG has the advantage of alterable chain length to accommodate specific needs. Previous studies [23, 27,28] have shown that about 1 mole % of PEG lipids of adequate polymer size can completely cover a lipid bilayer surface to provide total inhibition of liposome-cell adhesion. This percentage of PEG-lipids is generally much lower than that commonly used to make stealth liposomes (5–15 mole %) in in vivo applications. However, uncovering or de-stealthing of the PEG coated liposomes at the desired sites has proven to be difficult to achieve.

In recent years poloxamers, a group of tri-block co-polymers, have also been used to sterically stabilize liposomes [9–11]. Poloxamers (sometimes called Pluronics), are polyethylene oxide (PEO)—polypropylene oxide (PPO)—polyethylene oxide tri-block co-polymers of different molecular weights. The hydrophobic PPO group in the middle links the two hydrophilic PEO groups. The amphiphilic nature of the poloxamers makes them extremely useful in various applications as emulsifiers and stabilizers [12]. In an aqueous environment, poloxamers at a given concentration remain as individual (non-associated) co-polymers (referred to herein as 'monomers'), at temperatures below their critical micellar temperature (CMT). Above the CMT the molecules become more lipophilic, and form micelles with hydrophobic PPO groups at the core of the micelle. Poloxamers of different molecular weights and with different hydrophil-lipophil balance (HLB) have different CMTs [13]. This monomer-to-micellar transition process is extremely temperature-sensitive. With a small change of temperature, the corresponding critical micellar concentration (CMC) may change by several orders of magnitude [14].

Several studies have been conducted regarding the interaction of poloxamers with liposomes [15–17]. Moderate to severe structural changes in liposomes were observed using cryo-transmission electron microscopy [18]. As observed by techniques like NMR [17], dynamic light scattering [15–17] and differential scanning calorimetry [19], poloxamers can either be incorporated in or adsorbed on the liposome surface to cause steric stabilization.

Although poloxamers have been used for stabilizing liposomes, no method is available on utilizing the thermal properties of poloxamers to manipulate liposome-cell adhesion resulting in enhanced retention of sterically protected liposomes at or near the target site.

SUMMARY OF THE INVENTION

The present invention provides a method for targeted delivery of agents comprising the steps of providing a mixture of poloxamer molecules, and liposomes encapsulating the delivery agent; heating the mixture to above the critical micellar temperature (CMT) for the poloxamer, so as to allow a fraction of the poloxamer molecules to form micelles and another fraction of the poloxamer molecules to become incorporated into the liposomes; administering the heated mixture to an individual; and cooling the target site to below the CMT so as to cause the poloxamer molecules forming the micelles and incorporated into the liposomes to dissociate into monomers thereby exposing the liposomal adhesion sites causing the liposomes to be retained at or near the target site.

The present invention also provides a liposomal composition for targeted delivery of agents comprising poloxamer molecules and liposome vesicles encapsulating one or more agents for delivery, wherein upon heating of the composition to above the CMT, a fraction of the poloxamer molecules form micelles and another fraction of the poloxamer molecules become incorporated into the liposomes resulting in stealthing of the liposomes such that the liposomal-cell adhesion is reduced, and wherein upon cooling the mixture at the target site to below the CMT of the poloxamer, the poloxamer molecules become dissociated into monomers to expose cell-adhesion sites thereby causing retention of the liposomes at or near the target site. In one embodiment, the poloxamer Pluronic F127 (M.W.~12,600, $PEO_{98}$- $PPO_{67}$- $PEO_{98}$) is used.

DETAILED DESCRIPTION OF THE INVENTION

Figure 1:
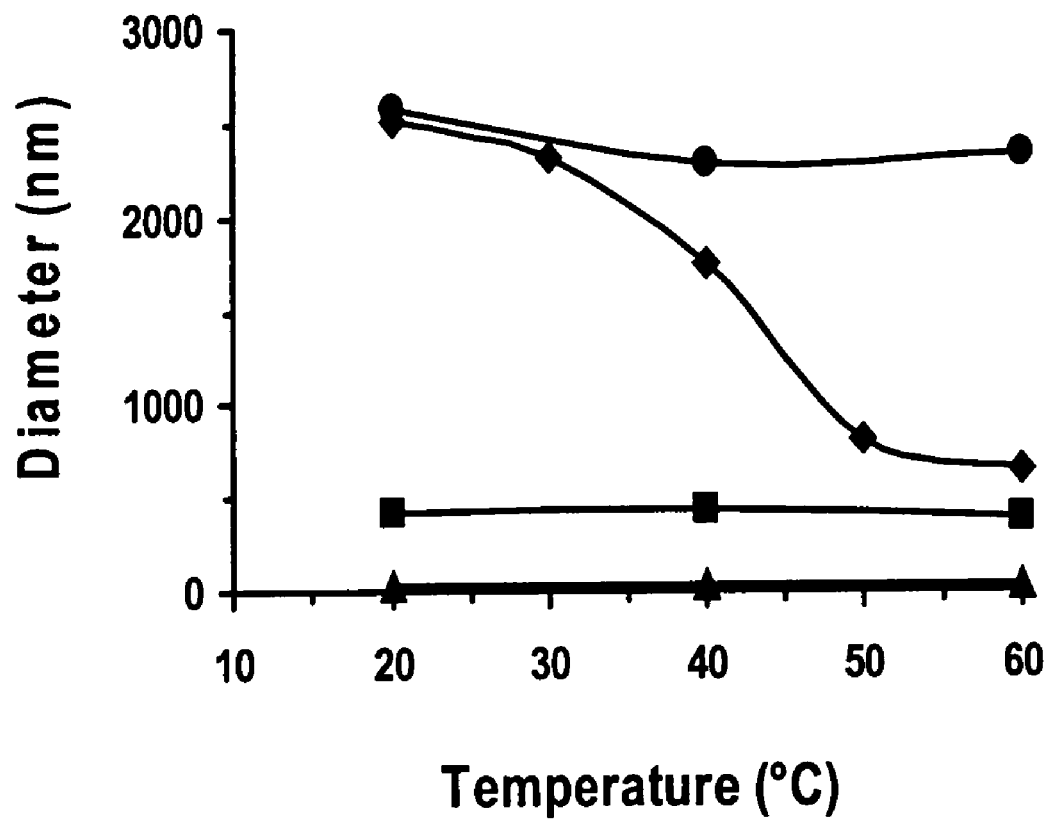
FIG. 1 is a representation of the change in vesicle size with temperature, as determined using Quasi-elastic light scattering (QLS). All vesicles are made of EPC and 0.032% (w/v) Pluronic F127 except the control sample which has no F127: MLV (diamond), LUV (square), SUV (triangle) and control MLV (circle).

Definitions:

The term "liposomes" or "vesicles" or "liposome vesicles" as used herein means structures having lipid containing membranes enclosing an aqueous interior. Structures having more than one layer of membranes are termed multilamellar vesicles (MLVs). Structures having one layer of membrane are termed unilamellar vesicles. The unilamellar vesicles may be large unilamellar vesicles (LUVs) or small unilamellar vesicles (SUVs).

The term "large unilamellar vesicles" or "LUVs" as used herein means unilamellar vesicles having a diameter of between about 100 nm to 1.0 $\mu$m.

The term "small unilamellar vesicles" or "SUV" as used herein means unilamellar vesicles having a diameter of less than 100 nm. Most SUVs typically have a diameter of about 30 nm.

The term "critical micellar temperature" or "CMT" as used herein means the temperature above which the polymer molecules by themselves exist in aqueous medium as micells, and below which the polymer molecule by themselves exist as individual molecules (unimers) in solution.

The term "poloxamer" as used herein means block co-polymers of polyethylene oxide (PEO)—polypropylene oxide (PPO)—polyethylene oxide (PEO), each block can be of different molecular weights.

The term "Delivery Agent" as used herein means any chemical compound that is encapsulated in the LUVs for delivery to a target site. Examples of Delivery Agents are provided below.

The term "Stealthing" as used herein means a process of coating the surface of liposomes with a layer of poloxamer molecules that enables the liposomes to avoid being removed from the circulation system of the body by the mononuclear phagocytic system of the body, thus prolonging their circulation time as compared to that of non-coated liposomes.

The term "De-stealthing" as used herein means the process of removing the protective coating that causes the stealthing of liposomes as described above.

The present invention provides a composition and method for temperature sensitive stealthing and de-stealthing of liposome vesicles. The composition comprises (1) liposomes encapsulating one or more Delivery Agents; and (2) a plurality of poloxamer molecules, wherein upon increasing the temperature to above the CMT of the poloxamer, the liposomes become stealth and upon cooling to below the CMT, the liposomes are de-stealthed allowing the adhesion of liposomes to cells.

The lipids useful for preparing liposomes include but are not limited to phospholipids such as phosphatidylcholine, phosphatidylserine, phosphatidylglycerol, phosphatidylethanolamine, phosphatidylinositol and their mixtures, and with added sphingolipids, glycolipids, fatty acids and cholesterol at various proportions if desired.

The polymer useful for this invention is poloxamer (Pluronics). Poloxamers are polyethylene oxide (PEO)—polypropylene oxide (PPO)—polyethylene oxide triblock co-polymers of different molecular weights. The hydrophobic PPO group in the middle links the two hydrophilic PEO groups. The hydrophilic PEO groups of a poloxamer, on either side of the central PPO unit, can provide steric protection to a bilayer surface. Although not intending to be bound by any particular theory, it is considered that the central PPO unit, being hydrophobic, would tend to push into the bilayer interior serving as an anchor. Dislodging the poloxamer molecule from the bilayer is achieved by reducing its hydrophobicity. Hydrophobicity is reduced by decreasing the temperature. In an aqueous medium, poloxamers stay as individual molecules at temperatures below their CMT, but at temperatures above the CMT, individual molecules are forced to form micelle to shield the lipophilic PPO units from the aqueous environment. In the presence of lipid bilayers, some poloxamer molecules would partition into the bilayers in addition to forming micelles with other poloxamer units. If the temperature again goes below the CMT, the poloxamer molecules dislodge themselves from the bilayers or micelles to become individual molecules again. Suitable poloxamers for the present invention are those that will have: a) a large enough PEO (about 50 to 100 units) to cause complete stealthing; b) an optimum size PPO (about 20 to 60 units) which would provide enough anchoring to attach to the membrane; and most importantly, c) a CMT value around the physiological temperature (i.e. between about 33° C. to 43° C., preferably around 37° C.) corresponding to a relatively small concentration (0.01 to 1% w/v) of the poloxamer to make it useful in the in vivo conditions Pluronic F127 (M.W.~12,600, $PEO_{98}$- $PPO_{67}$-$PEO_{98}$) is an example of a suitable poloxamer. Other poloxamers satisfying these criteria include but are Pluronic F87, F88, F 98, F108, and P188. The liposomes of the present invention are used as delivery vehicles and can be prepared by standard techniques. For example, lipid components (such as phopatidylcholine and cholesterol) in chloroform are mixed and dried to form a lipid film. The film is rehydrated in the presence of the drug to form MLVs. Small unilamellar vesicles (SUVs) can be prepared from the MLVs by standard techniques such as sonication and LUVs can be made by extrusion. Vesicles may also be made by other methods such as reversed phase evaporation, detergent dialysis and freeze-thawing. The LUVs and SUVs are separated from the free agent and poloxamer by standard techniques such as filtration or dialysis. The filtration method entails passing the sample through a filter device (such as Millipore® filter) with the filter pore size smaller than the SUV or LUV, such that vesicles are retained behind the filter while free agents and poloxamers are filtered through. The dialysis method entails enclosing the sample within a dialysis bag or device, with the membrane pore size smaller than the SUV or LUV, such that free agents and poloxamer molecules may diffuse through to the dialysis medium, and vesicles are retained. In addition, veiscles may be separated from free agents and poloxamer molecules s by size exclusion column chromatography. MLV can be separated by differential centrifugation.

The agents that can be delivered by the liposomal composition of the present invention include therapeutic drugs, pharmacologic active agents, nutritional molecules, diagnostic agents, image contrast agents and any other molecules that is desired to be delivered to a particular physiological site. Therapeutic agents include antibiotics, anti-tumor agents, anti-inflammatory agents, anti-neoplastic agents, anti-microbial agents, anti-viral agents, immunosuppressive agents, antisense oligonucleotides, plasmids, enzymes, hormones, nanoparticles and the like. When the delivery agents are small in size (such as nanoparticles), delivery vehicles including, but not limited to, micelles, hydrophobic beads or colloidal particles, can be used instead of liposomes. The stealthing and de-stealthing of the delivery vehicles is similar to the liposomes.

Liposomes of the present invention can be administered using methods that are well known in the art. The liposomes of the present invention are stealth when they are maintained at temperatures above the CMT (in the case of F127 at 0.03% w/v, it is above 35° C.). The methods of administration include delivery of the liposomal composition to the bloodstream by intravenous administration or direct delivery to the target site. For example, the liposomal composition may be delivered directly to the target site such as a tumor or a site of inflammation. Suitable concentration of the poloxamer are between about 0.01% to about 0.2%.

Once liposomes have been delivered to the site either via normal blood flow or by direct administration at the site, the target site is cooled below the CMT which is variable and adjustable according to the poloxamers used and the concentration. In the case of F127 at 0.03%, it is 35° C.)

Figure 5:
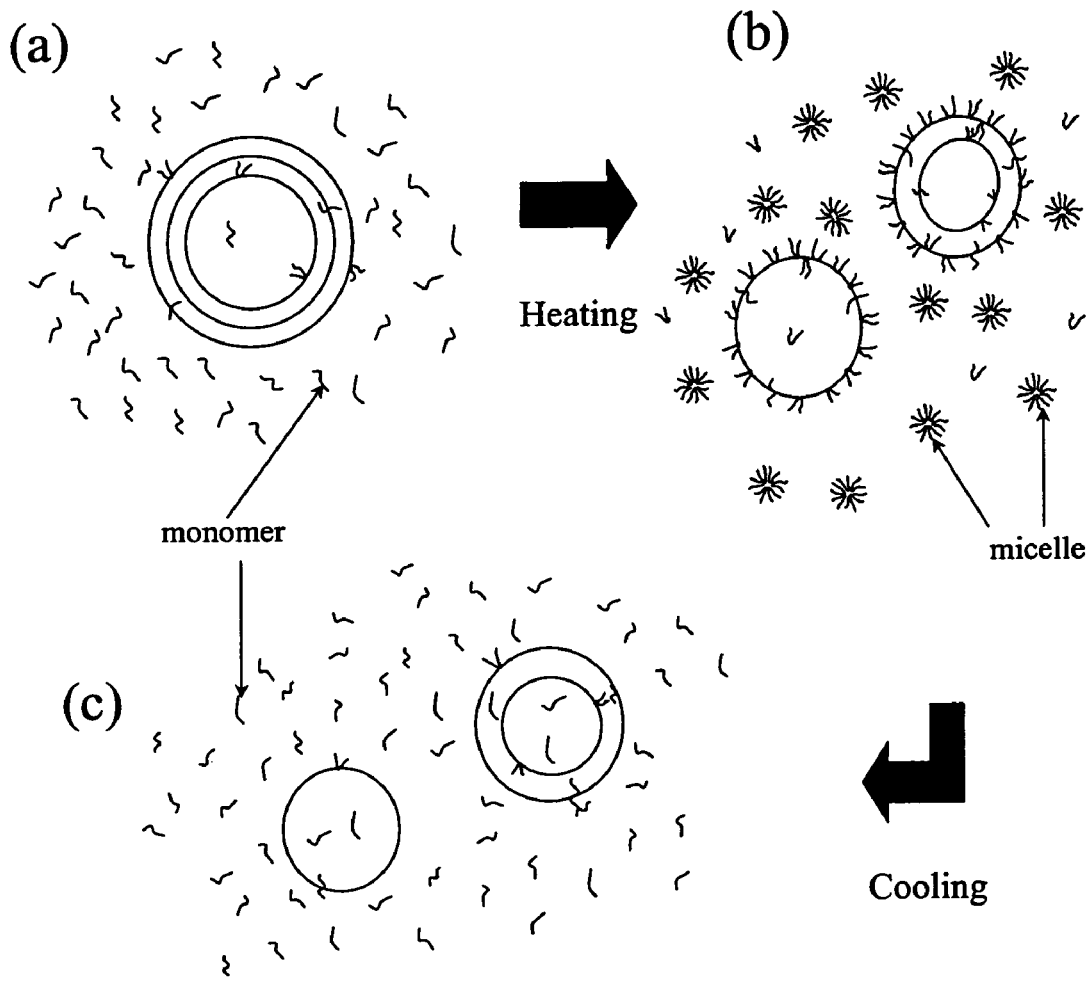
FIG. 5 is a schematic illustration of the proposed fate of EPC, in the presence of Pluronic F127, during thermal cycling: (a) at 4° C., larger MLVs with few individual Pluronic F127 molecules associated with the liposomes and most individual molecules floating outside the liposomes; (b) at a temperature above the CMT (e.g. 41° C.), smaller size liposomes with many surface-associated Pluronic F127 and presence of Pluronic F127 micelles outside the liposomes; (c) when cooled down below the CMT (e.g. 4° C.), liposome size remains the same with individual Pluronic F127 molecules present all around.

The overall method of the present invention is illustrated in a cartoon of FIG. 5 This cartoon shows the initial stage of the process when MLVs are formed. At 4° C., the poloxamer molecules (Pluronic F127) are individual molecules. Few of the poloxamer molecules are present in the liposomes—inside the aqueous core or in the lamellae. The individual molecules (monomers) incorporated into the lipid bilayers of the liposomes can be either trans-lamellar or anchored to the bilayer from one side. Most of the individual poloxamer molecules are floating outside the liposomes. When these MLVs are heated to a temperature (say 41° C.) above the poloxamer CMT, poloxamer molecules would form micelles (FIG. 5b). Also, there is be increasing number of poloxamer molecules associated with the liposome, since the hydrophobicity of the molecules has increased. MLV size would go down considerably due to breaking up of the outer wall of MLV, in accordance with the results of the liposome size measurement. Micelles could also be present in the liposome core. When these hot liposomes are cooled below the CMT, poloxamer micelles become individual molecules again and leave the liposomes with low polymer shielding (FIG. 5c).

The present invention will be better understand from the following embodiments which are intended to be illustrative and not restrictive in any way.

EXAMPLE 1

This embodiment describes the preparation of liposomes useful for the present invention. To illustrate this embodiment the preparation of liposomes with EPC and Pluronic F-127 is described. All the lipids, i.e., egg phospatidylcholine (EPC), di-oleoyloxy-trimethylammonium propane methyl sulfate (DOTAP), di-palmitoyl Rhodamine phosphatidylethanolamine (DPRhPE) and di-stearoyl(polyethylene glycol 5000) phosphatidylethanolamine (PEG5000-DSPE) were purchased from Avanti Polar Lipids Inc. (Alabaster, Ala.). The lipids were stored at $-80°$ C.

All liposomes were made with EPC and different mole (or weight) % of Pluronic F127. Multi lamellar vesicles (MLV), large unilamellar vesicles (LUV) and small unilamellar vesicles (SUV) were made for different experiments. Pluronics were either co-solubilized with the lipid during preparation of liposomes or added afterwards to the already formed liposomes. For cell adhesion experiments, DOTAP and DORhPE were added to make the liposomes.

Lipids, in chloroform, were mixed in a round-bottomed flask and dried under a gentle stream of nitrogen gas to form a thin layer on the flask wall by well known methods. The film was dried further in a vacuum dessicator, for 3 to 4 hours, to remove any remaining solvent. MLVs were formed by first re-suspending the dry lipid film with de-ionized water, or buffer, followed by vortexing. SUVs were formed by sonicating the MLV solution in a bath type sonicator (Laboratory Supplies Co., Hicksville, N.Y.). Sonication was done under a nitrogen atmosphere, for 10 min. or more, until the solution turned clear. LUVs were formed by extruding the MLV solution through a 0.4 $\mu$m poly-carbonate filter (Millipore, Bedford, Mass.), for fifteen times or more. All liposomes were prepared and kept inside a cold room (4° C.), such that the liposomes and poloxamers are kept well below the CMT of the poloxamer used before using in the experiment.

EXAMPLE 2

This embodiment describes the effect of poloxamer, in this example, Pluronic F-127, on the size of the EPC vesicles during temperature change. To illustrate this embodiment, MLVs comprising EPC, DOTAP and DPRhPE were made as described in Example 1. All samples were made, at 4° C., with EPC and 8 mole % DOTAP. The "control" MLVs did not have any Pluronic F127 while the "F127" MLVs had 0.03% (w/v) Pluronic F127 in the sample environment.

The lipid concentration of each sample was 1.1 mg/ml and final Pluronic F127 concentration in the liposome solution was 0.032% (w/v). All the samples were made at 4° C. The temperature was gradually cycled from 4° C. to 41° C. to 4° C. during measurement. During the experiment, the sample to be measured was kept at the desired temperature by a Peltier unit of the QLS machine. Each sample was kept in the sample chamber for at least 15 minutes, to achieve thermal equilibrium, before starting measurement. All the other samples, used in the same experiment, were kept at their respective desired temperatures in water baths.

Liposome sizes were measured by quasi-elastic light scattering (QLS), using a model 370 sub-micron particle sizer (Nicomp Particle Sizing Systems, Santa Barbara, Calif.). The particle sizer was calibrated with polystyrene latex spheres (Interfacial Dynamics Corporation, Portland, Oreg.) of sizes between 30 and 2980 nm and was found accurate for all diameters. An argon ion laser, with a maximum CW output of 2W, was used as the light source. The photon counts were always adjusted to about 300 kHz. Size of liposomes was analyzed by multi-modal NICOMP vesicle analysis program. The volume-weighted mean vesicle diameter was used for all our experimental purposes. Viscosity and index of refraction values of the medium were adjusted to allow for the change with changing temperature. QLS was also used to determine the micellar size of the Pluronic in an aqueous environment. FIG. 1 shows the result of the dynamic light scattering experiment. The control sample contains MLVs made of EPC only. The other three samples: MLV, LUV and SUV are all made of EPC and 1 mole % (0.03% w/v) Pluronic F127. The initial diameter of the "control", MLV, LUV and SUV samples was 2.58 $\mu$m, 2.52 $\mu$m, 0.43 $\mu$m and 34 nm, respectively. As shown in FIG. 1, "control" sample diameter does not decrease much over the whole temperature range of 20 to 60° C., ending at 2.34 $\mu$m, a decrease to 91% of the initial size. The MLV sample diameter does not decrease significantly at 30° C. But at 40° C. it decreases to 1.75 $\mu$m, which is 70% of the initial diameter. From 40° C. to 50° C., the size reduces even further to a diameter of 0.81 $\mu$m (32%). At 60° C. the diameter is 0.65 $\mu$m. The LUV diameter reduces slightly to 0.39 $\mu$m, about 90% of the low temperature value. SUV sample size remains more or less same throughout the temperature range. Thus, the presence of 1 mole % Pluronic F127 seems to affect the MLV sample most, decreasing its diameter to 26% of the initial value over this temperature range.

Average diameter of a Pluronic F127 micelle, as determined by QLS, is 23 nm. The size of MLV containing 8 mole % DOTAP, with or without Pluronic F127, was also measured. Result of the size measurement experiment of EggPC/DOTAP MLVs is presented in Table 1. The experiment was performed at two temperatures: 4° C. and 41° C. For both the temperatures, size of the "F127" DOTAP-MLVs is larger than that of the "control" DOTAP-MLVs. There is an average increase of 23% and 15% in the diameter of the "F127" samples over those of the "control" samples, respectively at 4° C. and 41° C. All DOTAP containing MLVs are smaller than their counterpart without DOTAP (FIG. 1).

Another method to estimate vesicle size in the presence of F127 was also used. Sample turbidity provided an estimation of vesicle size changes. Static (90°) light scattering, at 600 nm was used to measure the turbidity i.e. relative scattering intensity (which corresponds to the size) of the liposomes at different temperature points with a SLM 8000 (SLM Instruments Inc., Urbana, Ill.) fluorimeter. Turbidity measurement (data not shown) supports the QLS size determination, showing similar trend in size reduction of the vesicles upon heating. These results also show that liposome sizes remain same even when the samples are cooled down, indicating that there is no significant aggregation during the cooling process.

The temperature dependent liposome size changes show that at the concentration of 0.032% (w/v), used in our experiment, Pluronic F127 causes significant size reduction of the MLVs at temperatures above the CMT. Moreover, the turbidity measurement shows that upon cooling, the size of the vesicles remain the same. This suggests that cooling does not have any further detrimental effect such as aggregation or destabilization. Johnsson et al. reported a reduction in size of the MLVs by Pluronics, at temperatures above the CMT, interpreting this as a disruptive effect by the polymer at those temperatures [18]. In the present invention, using different methods, similar effects were observed. Much lower concentration of the poloxamer was used in the present invention in comparison to that used by the Johnsson et al. The disruption is not complete at the poloxamer concentration used, and the poloxamer has no significant effect on LUV and SUV (FIG. 1).

EXAMPLE 3

This embodiment demonstrates visualization of association of Pluronic F-127 with liposomes at different temperatures. The negative-stain electron microscopy of the Pluronic-containing liposomes was used to examine the association of the Pluronic with liposomes at different temperatures. EPC liposomes, with or without 1 mole % (0.03% w/v) Pluronic F127, were prepared and then temperature treated, as described herein. Pluronic 127 at a concentration of 0.03% (w/v) has a CMT of about 35° C. Negative staining samples were prepared below CMT (4° C.) and above CMT (41° C.) to observe the behavior of Pluronic F127 molecules in the presence of lipid vesicles at two significantly different temperature conditions. The temperature treated liposomes were used as samples for negative staining.

Figure 2:
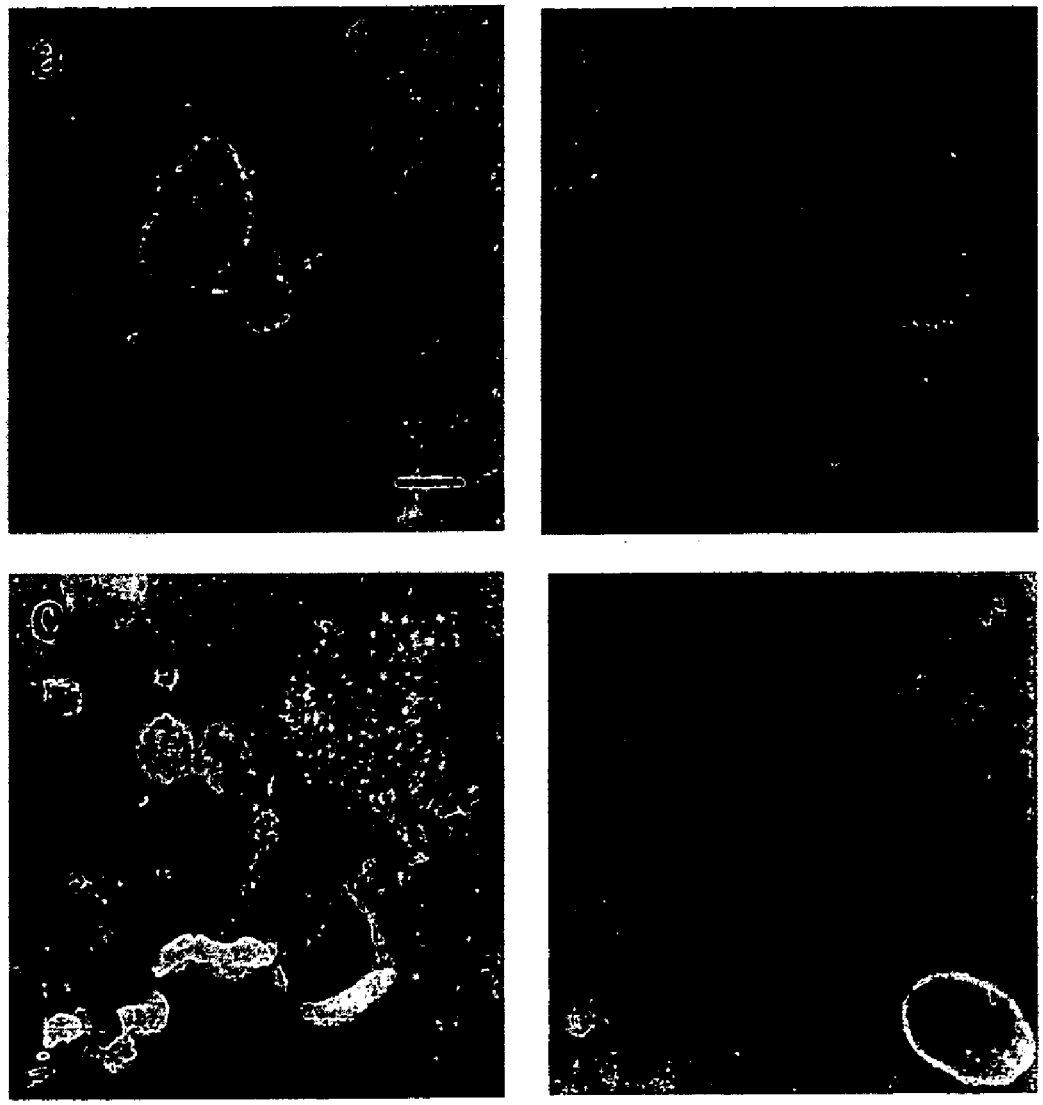
FIG. 2 is a representation of the negative stain electron micrographs: the control MLV samples (a, b) are made of EPC only, while the F127 MLV samples (c, d) are made of EPC with 0.032% (w/v) Pluronic F127. Micrographs (a) and (c) are of samples made at 4° C. and micrographs (b) and (d) are of samples made at 41° C. Presence of individual Pluronic molecules (small white dots) in (c) and micelles (fluffy white structures) in (d) are indicated by arrowheads. Scale bar is 100 nm.

The results are presented in FIG. 2 which consists of micrographs showing images of negative stained EPC MLVs at different temperatures. FIG. 2 (a, b) are control samples consisting of EPC MLVs only while FIG. 2 (c, d) are F127 samples consisting of EPC MLVs with 0.03% (w/v) Pluronic F127. FIG. 2(*a*, c) show samples made at 4° C., while the samples seen in FIG. 2(*b*, d) are made at 41° C. FIG. 2(*a*) shows vesicles with an even background. FIG. 2(*c*), in contrast, shows vesicles with tiny white dots in the background. The size of these dots on average are about 10 nm diameter and roughly correspond to the size of the individual Pluronic F127 molecules in aqueous solution. The diameter of individual Pluronic F127 molecules, based on the calculation of its radius of gyration [24], was 7 nm. FIG. 2(*b*) again shows vesicles with smooth background. FIG. 2(*d*) shows one vesicle at the lower right hand corner, and fluffy white structures over the background area. These fluffy structures are larger than the white dots seen in FIG. 2(*c*). Again, average size of these structures (44 nm diameter), though somewhat higher, correspond to the size of the Pluronic F127 micelles (23 nm) as measured by quasi-elastic light scattering technique. These experiments support the size determinations of Example 2.

EXAMPLE 4

This embodiment describes the determination of the amount of Pluronic associated with liposomes as a function of temperature. EPC MLVs were made at 4° C. and a concentrated (60 mg/ml) aqueous Pluronic solution was added to the MLVs to make the F127 concentration in the solution about 0.75% (w/v). Pluronic was added after the formation of the liposomes to ensure that no Pluronic was present inside the liposomes. One third of the samples were kept at 4° C. ("cold" samples), while the remaining were kept at 41° C. After 30 minutes, half of the samples at 41° C. were brought back to 4° C. ("thermally cycled" samples). The samples kept at high temperature were used as the "hot"

samples. Thermally cycled samples were kept in cold condition for 30 min to attain thermal equilibrium. Each sample was then diluted ten times (i.e. 1:10), using distilled water, and centrifuged for 20 min at 15,700×g. A pellet formed at the bottom of the centrifuge tube. The supernatant was carefully removed, using a micro-pipette, so as not to disturb the pellet, and stored for further analysis. Dilution, centrifugation and supernatant removal was done in cold conditions (4° C.), for the "cold" and "thermally cycled" samples, or hot conditions (41° C.), for the "hot" samples. 40 μl of 10% Triton X-100 and 160 μl distilled water was added to each pellet and vortexed to thoroughly dissolve the pellet into a solution. These pellet and supernatant solutions were used for the assay of Pluronics.

An assay for Pluronics originally developed by Greff et al. [20], and modified by Tercyak and Felker [21] was further modified by the formation of a complex of Pluronic with cobalt thiocyanate. The absorbance of the solubilized complex was measured spectrophotometrically and used as a quantitative measure as described for Pluronic F68 [22]. Briefly, 100 μl cobalt thiocyanate solution, 200 μl ethyl acetate and 80 μl of absolute ethanol were added to 200 μl Pluronic F127 standard (or a sample containing unknown amount of Pluronic). The resulting suspension was mixed well, in a 1.5 ml eppendorf centrifuge tube, by mild vortexing and then centrifuged for 2 min at 15,700×g. After centrifugation, the supernatant was carefully removed without disturbing the pellet. The pellet and tube walls were carefully washed with 200 μl of ethyl acetate, several times, until the aspirated ethyl acetate became colorless. The pellet was thoroughly dissolved in 2 ml acetone by vortexing and the absorbance was measured using a Zeiss spectrophotometer (Brinkmann Instruments, NY) at 328 nm. The concentration of Pluronic in the unknown samples was determined using a calibration curve. Absorbance measurements were carried out in triplicate for all the standard dilutions and unknown samples.

Figure 3:
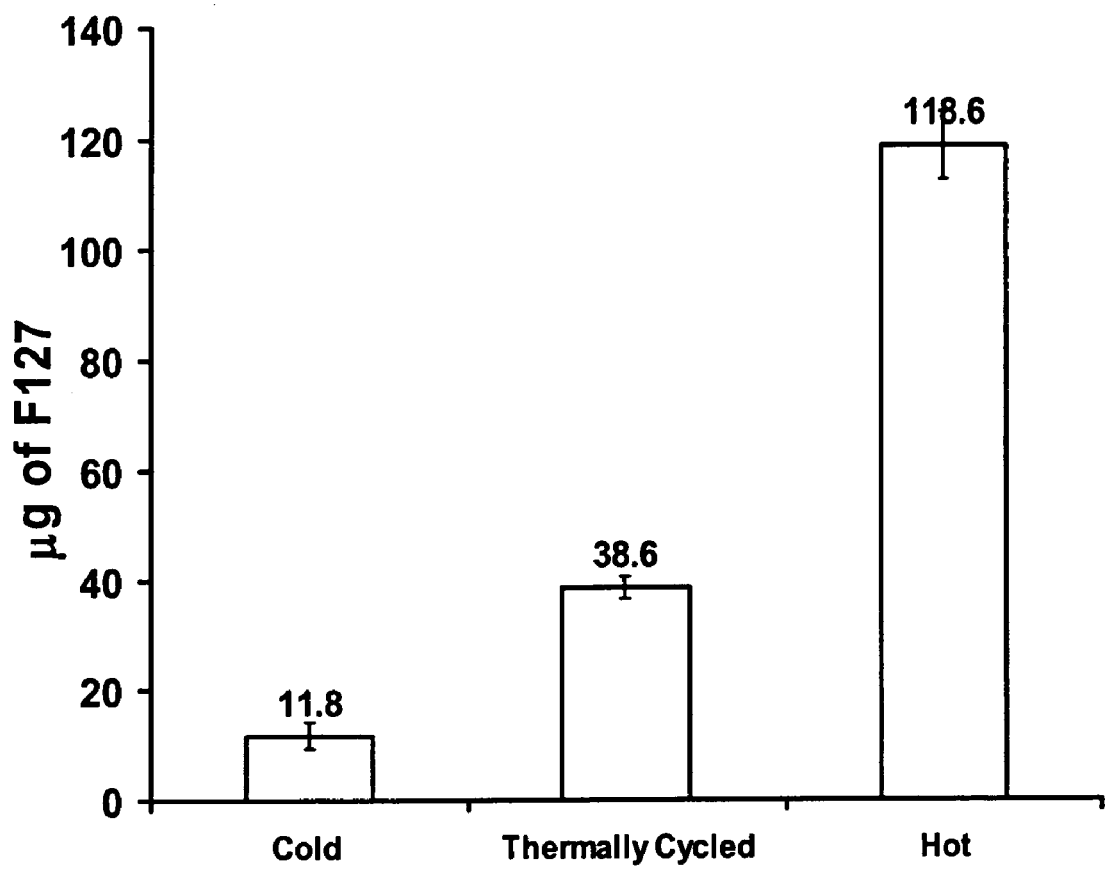
FIG. 3 is a representation of the amount of Pluronic F127 associated with liposomes in a sample, as determined by the Pluronic Assay. The three different samples are: Cold, Thermally cycled and Hot. The number above each sample point represents $\mu$g of Pluronic F127 for the corresponding sample. Error bar represents variations among at least three repeating samples.

The results are shown in FIG. 3 which shows the amount of Pluronic F127 associated with the liposomes of different samples. The three samples shown are pellets obtained from the "cold", "thermally cycled" and "hot" samples. The primary data obtained from the experiment were O.D. (optical density) values, which were converted to μg of F127, using a calibration curve. The amount of F127 present in the "cold", "thermally cycled" and "hot" sample are 11.8, 38.6 and 118.6 μg, respectively. The results show that the "hot" sample retains 10-fold more Pluronic than the "cold" sample, and 3-fold more than the "thermally cycled" one. These results demonstrate that the association of pluronics with the liposomes is significantly greater at temperatures higher than the CMT of the pluronics at that concentration.

EXAMPLE 5

This embodiment demonstrates the effect of poloxamers on adhesion of liposomes to cell surfaces at different temperatures. CHO cells were grown in F-10 medium plus 13% NCS at 37° C. and 5% $CO_2$. All cells were passaged twice weekly. Cells were seeded at a concentration of $1 \times 10^6$ cells per well in 12 well plates. The cells were allowed to grow for 24 h, reaching approximately 80% confluency, before experimentation. Cells were washed twice with F-10 medium and incubated at cold (4° C.) or hot (41° C.) condition for 20 minutes before adding 100 μl liposome solution to each well. MLVs of EPC with 8 mole % DOTAP, 1 mole % DPRhPE and 1 mole % Pluronic F127 were used. Control samples did not have any Pluronic in them. Since 0.75 mole % PEG5000 conjugated lipid is generally sufficient to inhibit cell adhesion to bilayer surface [23], liposomes were made with 1 mole % PEG5000-DSPE, instead of 1 mole % Pluronic, to serve as positive control. The liposome solutions were treated with cold and/or hot conditions for 20 minutes or more. After adding liposome solution to the wells, they were incubated at respective temperatures. The cells were washed twice with PBS to remove any non-adhering liposomes. Cells from each well were scraped into a cuvette. PBS solution was added to the cells to make a total volume of 3 ml. Fluorescence intensity of the resulting suspension was measured with an excitation wavelength of 550 nm and an emission wavelength of 590 nm using a SLM 8000 fluorimeter.

Figure 4:
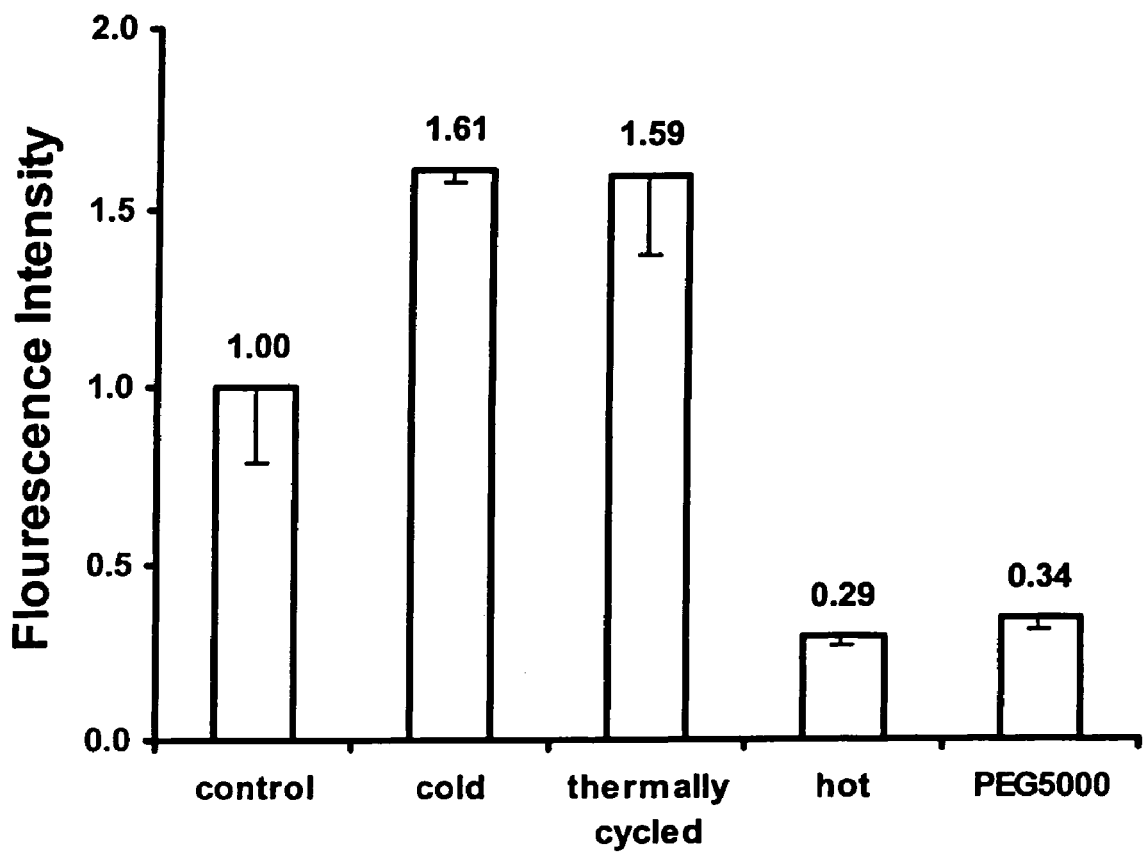
FIG. 4 is a representation of the association of fluorescently labeled MLVs to CHO cells: all samples are made of EPC, 8 mole % DOTAP and 1 mole % DPRhPE. Additionally, the cold, thermally cycled and hot samples have 0.03% (w/v) Pluronic F127, while the PEG5000 sample has 1 mole % PEG5000-DSPE. The number above each sample point represents the fluorescence intensity value for the corresponding sample. Error bar represents variations among at least three repeating samples. All samples are normalized against the control sample.

FIG. 4 shows the result of association (adhesion plus internalization) of fluorescently labeled liposomes with CHO cells. The lipids used for this experiment were EPC with 8 mole % DOTAP and 1 mole % fluorescent lipid DPRhPE, with or without 1 mole % Pluronic F127. DOTAP at 8 mole % was the optimum amount to facilitate adhesion without suppressing the inhibitive effect of liposome-cell adhesion by Pluronic F127. The control sample was without F127. The samples marked "cold", "thermally cycled" and "hot" were with F127, as described in the last section, while the sample marked "PEG5000" was made with 1 mole % of PEG5000-DSPE, instead of the F127 (positive control). All the fluorescence intensity values were normalized against the respective (hot or cold) "control" values. After normalization, the "thermally cycled" sample, with a fluorescence reading of 1.59, is as fluorescent as the "cold" sample (1.61). The "hot" sample, on the other hand, has as low fluorescence intensity as that of the "PEG5000" sample. The normalized fluorescence intensity values of 0.29 and 0.34 for "hot" and "PEG5000" samples, respectively, are significantly lower than the fluorescence intensity value of the "control" sample, showing inhibition to the adhesion of liposomes to the cell surfaces. This experiment demonstrates that retention of the liposomal compositions of the present invention can be increased at target sites by reducing the temperature.

Modifications of the present invention apparent to those skilled in the art are intended to be within the scope of the invention as described in the specification and claims.

REFERENCES

[1] M. C. Woodle, D. D. Lasic, Biochim. Biophys. Acta 1113(2) (1992) 171–199.
[2] G. Blume, G. Cevc, Biochim. Biophys. Acta 1146(2) (1993) 157–168.
[3] J. H. Senior, Crit. Rev. Ther. Drug Carrier Syst. 3(2) (1987) 123–193.
[4] T. M. Allen, C. Hansen, J. Rutledge, Biochim. Biophys. Acta 981(1) (1989) 27–35.
[5] A. Gabizon, D. Papahadjopoulos, Proc. Natl. Acad. Sci. U.S.A. 85(18) (1988) 6949–6953.
[6] J. R. Bogner, F. D. Goebel, Chapter 23 in Stealth Liposomes, D. Lasic, F. Martin (Eds.), CRC Press, Inc., Boca Raton, 1995.
[7] T. M. Allen, C. Hansen, F. J. Martin, C. Redemann, A. Yau-Young, Biochim. Biophys. Acta 1066(1) (1991) 29–36.
[8] A. L. Klibanov, K. Maruyama, V. P. Torchilin, L. Huang, FEBS Lett. 268(1) (1990) 235–237.
[9] M. Jamshaid, S. J. Farr, P. Kearney, I. W. Kellaway, Int. J. Pharm. 48 (1988) 125–131.
[10] M. C. Woodle, M. S. Newman, F. J. Martin, Int. J. Pharm. 88 (1992) 327–334.

[11] M. A. Khattab, S. J. Farr, G. Taylor, I. W. Kellaway, J. Drug Target. 3 (1995) 39–49.
[12] P. Alexandridis, Curr. Op. Colloid Int. Sci. 2(5) (1997) 478–489.
[13] P. Alexandridis, T. A. Hatton, Chapter 12 in Dynamic properties of interfaces and association structures, V. Pillai, D. O. Shah (Eds.), AOCS Press, Champaign, Ill., 1996.
[14] P. Alexandridis, J. F. Holzwarth, T. A. Hatton, Macromolecules, 27(9) (1994) 2414–2425.
[15] K. Kostarelos, P. F. Luckham, Th. F. Tadros, J. Liposome Res., 5(1) (1995) 117–130.
[16] K. Kostarelos, Th. F. Tadros, P. F. Luckham, Langmuir, 15(2) (1999) 369–376.
[17] K. Kostarelos, P. F. Luckham, Th. F. Tadros, J. Chem. Soc., Faraday Trans., 94(15) (1998) 2159–2168.
[18] M. Johnsson, M. Silvander, G. Karlsson, E. Katarina, Langmuir, 15(19) (1999) 6314–6325.
[19] J. D. Castile, K. M. G. Taylor, G. Buckton, Int. J. Pharm. 182 (1999) 101–110.
[20] R. A. Greff, A. E. Setzkom, W. D. Leslie, J. Am. Oil Chem. Soc. 45 (1965) 611–615.
[21] A. M. Tercyak, T. E. Felker, Anal. Biochem. 187(1) (1990) 54–55.
[22] H. Ghebeh, A. Handa-Corrigan, M. Butler, Anal. Biochem. 262 (1998) 39–44.
[23] H. Du, P. Chandaroy, S. W. Hui, Biochim. Biophys. Acta 1326 (1997) 236–248.
[24] P. Alexandridis, L. Yang, Macromolecules, 33(15) (2000) 5574–5587.
[25] T. M. Allen, A. Chonn, FEBS Lett. 223(1) (1987) 42–46.
[26] D. Papahadjopoulos, A. Gabizon, Ann. N.Y. Acad. Sci. 507 (1987) 64–74.
[27] M. C. Woodle, K. K. Matthay, M. S. Newman, J. E. Hadiyat, J. R. Collins, C. Redemann, F. J. Martin, D. Papahadjopoulos, Biochim. Biophys. Acta, 1105(2) (1992) 193–200.
[28] D. C. Litzinger, L. Huang, Biochim. Biophys. Acta, 1127(3) (1992) 249–254.

What is claimed is:

1. A composition for temperature controlled cell surface adhesion of liposomes comprising
a) poloxamer molecules; and
b) liposomes encapsulating a delivery agent,
wherein the concentration of the poloxamer in the composition is between 0.01% w/v to 0.2% w/v wherein the critical micellar temperature (CMT) of the poloxamer at a concentration between 0.01% to 0.2% is between 33° C. and 43° C. wherein at above the CMT of the poloxamer, a fraction of the poloxamer molecules forms micelles and another fraction of the poloxamer molecules becomes incorporated into the liposomal bilayers, wherein the concentration of the poloxamer is such that the incorporation of the poloxamer molecules into the liposomal bilayer does not make the liposome leaky, but is sufficient to inhibit the liposome from adhering to cell surfaces, and wherein at below the CMT, the poloxamer molecules are dissociated from the liposome into monomers, allowing the liposomes to adhere to cell surfaces.

2. The composition of claim 1, wherein the poloxamer is Pluronic 127.

3. The composition of claim 1, wherein the poloxamer is selected from the group consisting of F87, F88, F 98, F108, and P188.

4. The composition of claim 1, the delivery agent is a therapeutic agent.

5. The composition of claim 1, wherein the delivery agent is a diagnostic agent.

6. The composition of claim 1, wherein the liposomes comprise egg phospatidylcholine, di-oleoyloxy-trimethylammonium propane methyl sulfate, and di-palmitoyl Rhodamine phosphatidylethanolamine.

7. The composition of claim 1, wherein the CMT of the poloxamer is about 35° C.

8. The composition of claim 1, wherein the liposomes comprise phopholipids selected from the group consisting of phosphatidylcholine, phosphatidylserine, phosphatidylglycerol, phosphatidylethanolamine, phosphatidylinositol and combinations thereof.

9. The composition of claim 8 wherein the liposomes further comprises sphingolipids, glycolipids, fatty acids and cholesterol.

10. A method of enhancing the delivery of a delivery agent to a target site in an individual comprising the steps of:
a) administering the composition of claim 1 to the individual such that the composition reaches the target site; and
b) cooling the target site such that the temperature at or near the target site is below the CMT, thereby allowing the liposomes to adhere to the cell surfaces at or near the target site.

11. The method of claim 10, wherein the poloxamer is Pluronic 127.

12. The method of claim 10, wherein the poloxamer is selected from the group consisting of F87, F88, F 98, F108, and P188.

13. The method of claim 10, the delivery agent is a therapeutic agent.

14. The method of claim 10, wherein the delivery agent is a diagnostic agent.

15. The method of claim 10, wherein the liposomes comprise egg phospatidylcholine, di-oleoyloxy-trimethylammonium propane methyl sulfate and di-palmitoyl Rhodamine phosphatidylethanolamine.

16. The method of claim 10, wherein the target is a tumor.

17. The method of claim 10, wherein the liposomes comprise phopholipids selected from the group consisting of phosphatidylcholine, phosphatidylserine, phosphatidylglycerol, phosphatidylethanolamine, phosphatidylinositol and combinations thereof.

18. The composition of claim 17 wherein the liposomes further comprises sphingolipids, glycolipids, fatty acids and cholesterol.

* * * * *